United States Patent [19]

Belleau et al.

[11] Patent Number: 5,041,449
[45] Date of Patent: Aug. 20, 1991

[54] 4-(NUCLEOSIDE BASE)-SUBSTITUTED-1,3-DIOXOLANES USEFUL FOR TREATMENT OF RETROVIRAL INFECTIONS

[75] Inventors: Bernard Belleau, Westmount; Dilip Dixit, Roxborro; Nghe Nguyen-Ba, La Prairie, all of Canada

[73] Assignee: IAF BioChem International, Inc., Montreal, Canada

[21] Appl. No.: 546,676

[22] Filed: Jun. 29, 1990

Related U.S. Application Data

[63] Continuation of Ser. No. 179,615, Apr. 11, 1988, abandoned.

[51] Int. Cl.$^5$ .................. A61K 31/52; A61K 31/505; C07D 405/04; C07D 473/00
[52] U.S. Cl. .................................. 514/274; 514/265; 514/266; 544/276; 544/277; 544/313; 544/314; 544/317
[58] Field of Search .................... 544/313, 314, 317; 514/274

[56] References Cited

U.S. PATENT DOCUMENTS

| 4,041,037 | 8/1977 | Dvonch et al. | 544/317 |
| 4,415,573 | 11/1983 | Ochi et al. | 544/312 X |
| 4,960,773 | 10/1990 | Korbonits et al. | 514/234.21 |

FOREIGN PATENT DOCUMENTS

| 0337713 | 10/1989 | European Pat. Off. | 544/314 |
| 0026514 | 7/1972 | Japan | 544/277 |
| 0179118 | 11/1982 | Japan | 514/274 |
| 2063257 | 6/1981 | United Kingdom | 514/274 |

OTHER PUBLICATIONS

Norbeck, et al., Chemical Abstracts, vol. 113(3):24406q (1990).
Mitsuya et al., "3'-Azido 3'-Deoxythymidine (BW A509U): An Antiviral Agent that Inhibits the Infectivity and Cytopathic Effect of Human T-Lymphotropic Virus Type III/Lymphadenopathy-Associated Virus In Vitro", Proc. Natl. Acad. Sci., U.S.A., 82, pp. 7096-7100 (1985).
Mitsuya et al., "Inhibition of the In Vitro Infectivity and Cytopathic Effect of Human T-Lymphotropic Virus Type III/Lymphadenopathy-Associated Virus (HTLV-III/LAV) by 2', 3'-Dideoxynucleosides", Proc. Natl. Acad. Sci. U.S.A., 83, pp. 1911-1915 (1986).
Balzarini et al., "Potent and Selective Anti-HTLV-III/LAV Activity of 2',3'-Dideoxycytidinene, the 2',3'-Unsaturated Derivative of 2',3'-Dideoxycytidine", Biochemical and Biophysical Research Communications, 140 (2), pp. 735-742 (1986).
Baba et al., "Both 2',3'-Dideoxythymidine and its 2',3'-Unsaturated Derivative (2',3'-Dideoxythymidinene) are Potent and Selective Inhibitors of Human Immunodefficiency Virus Replication In Vitro", Biochemical and Biophysical Research Communications, 142(1), pp. 128-134 (1987).
Lin et al., "Synthesis and Antiviral Activity of Various 3'-Azido, 3'-Amino, 2',3'-Unsaturated, and 2',3'-Dideoxy Analogues of Pyrimidine Deoxyribonucleosides Against Retroviruses", J. Med. Chem., 30, pp. 440-444 (1987).
Herdewijn et al., "3'-Substituted 2',3'-Dideoxynucleoside Analogues as Potential Anti-HIV (HTLV-III/LAV) Agents", J. Med. Chem., 30, pp. 1270-1278 (1987).
Hallonquist et al., "Studies on Reactions Relating to Carbohydrates and Polysaccharides", Canadian Journal of Research, 7, pp. 129-136 (1933).
Corey et al., "Useful Procedures for the Oxidation of Alcohols Involving Pyridinium Dichromate in Aprotic Media", Tetrahedron Letters, 5, pp. 399-402 (1979).
Barton et al., "Transformations of Penicillin. Part III. A New Route to 2,2-Dimethyl-6α-Phenylacetamidopenam'α-Ols-Oxide and its Esters; O-NitroBenzoate as a Protecting Group for Alcohols and Phenols", J. Chem. Soc. Perkin I, pp. 599-603 (1973).
Wise et al., "Replacement of the 2-and 4-Oxo Groups of Uridine by a Seleno Group", Nucleic Acid Chemistry, pp. 413-419 (1978).
Ueda et al., "Synthesis and Optical Properties of 2,3-Dideoxy-D-Erythro-Hex-2-Enopyranosyl Nucleosides (Nucleosides and Nucleotides, LXII$^1$)", Chem. Pharm. Bull., 33(9), pp. 3689-3695 (1985).
Gosselin et al., "Systematic Synthesis and Biological Evaluation of α- and β-D-Lyxofuranosyl Nucleosides of the Five Naturally Occurring Nucleic Acid Bases", J. Med. Chem., 30, pp. 982-991 (1987).

Primary Examiner—Diana Rivers
Attorney, Agent, or Firm—James F. Haley, Jr.; Leslie A. McDonell

[57] ABSTRACT

There are provided novel 2-substituted-4-substituted-1,3-dioxolanes which are particularly useful as antiviral agents.

6 Claims, No Drawings

4-(NUCLEOSIDE BASE)-SUBSTITUTED-1,3-DIOXOLANES USEFUL FOR TREATMENT OF RETROVIRAL INFECTIONS

This is a continuation of application Ser. No. 179,615, filed Apr. 11, 1988 now abandoned, entitled 2-SUBSTITUTED-4-SUBSTITUTED-1,3-DIOXOLANES, SYNTHESIS AND USE THEREOF.

FIELD OF THE INVENTION

The present invention relates to novel 2-substituted-4-substituted-1,3 dioxolanes which are useful as antiviral agents.

PRIOR ART

Retroviral infections are a serious cause of disease and among others the acquired immunodeficiency syndrome (AIDS) is an immunosuppressive disease associated with life-threatening opportunistic infections and high susceptibility to unusual neoplasms (Kaposi sarcoma for instance). The human immunodeficiency virus (HIV) has been recognized as the etiologic agent of AIDS and compounds having an inhibitory effect against HIV multiplication have been actively sought.

One product which has been proposed for the treatment of AIDS is the 3'-azido-2',3'-dideoxy thymidine commonly referred to as AZT. The activity of this compound was disclosed by MITSUYA et al. in Proc. Natl. Acad. Sci., U.S.A. 1985, 82, 7096. The compound has the structure:

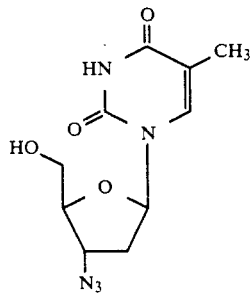

This compound is useful in protecting AIDS carriers against the cytopathogenic effect of the human immunodeficiency virus (HIV) which is the etiologic agent of AIDS.

Mitsuya et al. have also disclosed in Proc. Natl. Acad. Sci., U.S.A. 1986, 83, 1911 a group of 2'3'-dideoxynucleosides which appear to possess potent protective activity against HIV-induced cytopathogenicity. A typical such compound is the 2',3'-dideoxycytidine of the formula:

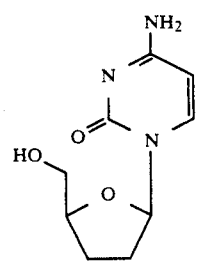

Balzarini et al. in Biochem. Biophys. Res. Comm. 1986, 140 735 disclose that the unsaturated analogue of the 2',3'-dideoxycytidine also possesses antiretroviral effectiveness. This unsaturated analogue has the formula:

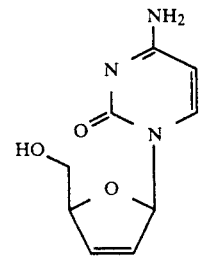

Baba et al. in Biochem. Biophys. Res. Comm. 1987, 142, 128 have described the 2',3'-unsaturated analogue of the 2',3'-dideoxythymidine which is a potent selective inhibitor of HIV replication and which corresponds to the formula:

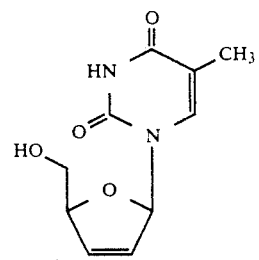

Analogues of the 3'-azido-2',3'-dideoxythymidine are the 3'-azido-2',3'-dideoxyuridine of the formula:

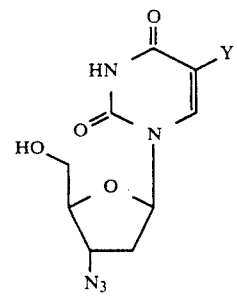

where y is bromine or iodine. These have been disclosed as having an inhibitory activity against Moloney murine leukemia by T. S Lin et al., in J. Med. Chem. 1987, 30, 440.

Finally, the 3'-fluoro analogues of the 2',3'-dideoxycytidine and of the 2',3'-dideoxythymidine have been disclosed by Herdewijn et al. in J. Med. Chem. 1987, 30, 1270 as having potent antiretroviral activity (anti-HIV). These analogues correspond to the formulae:

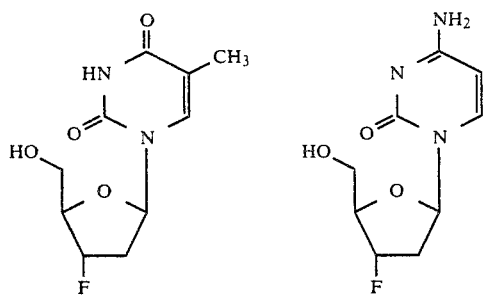

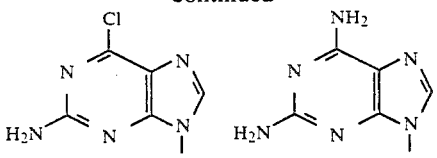

The most potent anti-HIV compounds thus far reported are 2',3'-dideoxynucleosides, more particularly, 2',3'-dideoxycytidine (ddCyd) and 3'-azido-2',3'-dideoxythymidine (AzddThd or AZT). These compounds are also active against other kinds of retroviruses (such as the Moloney murine leukemia virus). It is because of the increasing incidence and the life-threatening characteristics of AIDS that efforts are being expended to discover and develop new non-toxic and potent inhibitors of HIV and blockers of its infectivity.

It is therefore an object of the present invention to provide effective anti-HIV compounds of low toxicity and a synthesis of such new compounds that is readily feasible.

SUMMARY OF THE INVENTION

In accordance with the present invention there is provided novel 2-substituted-4-substituted -1,3-dioxolanes which are particularly useful as antiviral agents.

More specifically, the novel 2-substituted-4-substituted-1,3-dioxolane derivatives of the present invention correspond to the following formula (L):

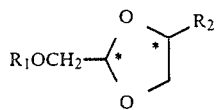

wherein $R_1$ is selected from H, an aliphatic acyl radical from 2 to 16 carbon atoms, a benzoyl which may be substituted in any position by a halogen, a lower alkyl, a lower alkoxy, nitro and trifluoromethyl groups and $R_2$ is a heterocyclic radical selected from:

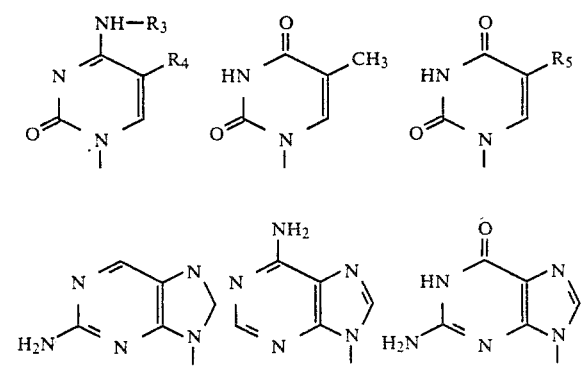

wherein $R_3$ and $R_4$ are respectively selected from H and a lower alkyl radical having from 1 to 3 carbon atoms, $R_4$ may also be an alkenyl radical and $R_5$ is selected from a lower alkyl or alkenyl radical having from 1 to 3 carbon atoms or a halogen selected from fluoro and iodo.

Also within the scope of the present invention are the 2,4-disubstituted-1,3-dioxolanes of Formula (L) wherein $R_2$ could be any nucleoside base analog, those base analogs being known by those skilled in the art of nucleoside chemistry.

There are two asymmetric carbons (asterisks) in the disubstituted 1,3-dioxolane molecule which provide for two racemic forms (±) and therefore four optical isomers. These racemates differ in the relative configurations of the 2- and 4-substituents which can either assume the cis- or trans-configurations. The use of a graphic representation of the 2,4-disubstituted-1,3-dioxolanes of Formula (L) is meant to include the dl racemic mixture as well as the separate d and l isomers thereof.

Also in accordance with the present invention, there is provided a pharmaceutical composition for administration to persons infected with the AIDS virus or other infectious agent which comprises a therapeutically effective amount of the 2,4-disubstituted dioxolane of Formula (L) or a pharmaceutically acceptable salt in association with a pharmaceutically acceptable excipient. The amount of active ingredient which is contained in a single dosage form will vary depending upon the host treated as well as the frequency and the mode of administration. Also within the scope of the present invention is a method for treating AIDS-infected persons which comprises administering to said persons a therapeutically effective amount of a 2,4-disubstituted-1,3-dioxolane of Formula (L). Also within the scope of the present invention is any combination of a 2,4-disubstituted-1,3-dioxolane of Formula (L) with another drug where such combination is therapeutically more advantageous than either drug given above.

DETAILED DESCRIPTION OF THE INVENTION

The compounds of the invention are prepared starting from glycerol and 2-halo- (or an equivalent leaving group such as aryl- or alkyl-sulfonyloxy) acetaldehyde preferably in the form of an acetal derivative according to the reported procedure of E.G. Hallinquist and H. Hibbert, Can J. Res. 1933,7, 129. For the purpose of this disclosure, the term acyl is an alkanoyl radical of 2 to 16 carbon atoms, e.g. acetyl, propionyl, isobutyryl, myristoyl, etc. The compounds of the instant invention are prepared by a total Synthesis comprising a few steps. The synthesis is practical and is commercially feasible. The process for preparing one specific compound of the present invention is outlined in the following Flowsheet 1:

Flowsheet 1

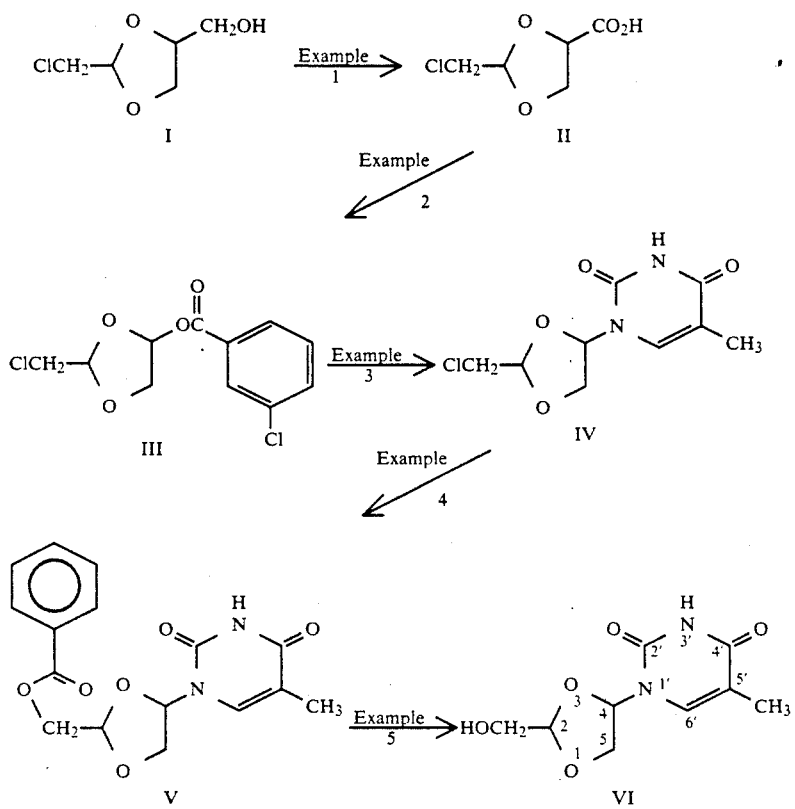

The various steps involved in the synthesis illustrated in Flowsheet 1 may be briefly described as follows:

Step 1: The primary alcohol function of the starting dioxolane is treated with an oxidizing reagent such as chromic acid (which may be complexed with pyridine) in a compatible organic solvent to give the corresponding dioxolane carboxylic acid II.

Step 2: The acid II is converted to a mixed anhydride using a alkyl chloroformate and submitted to a Bayer-Villiger oxidation with an organic peracid such as m-chloroperbenzoic acid to yield the corresponding aroyloxydioxolane III.

Step 3: Intermediate III is then reacted with thymine previously silylated with hexamethyldisilazane in a compatible solvent and the reaction catalyzed by a Lewis acid or preferably by trimethylsilyl triflate to give the thymin-1'-yl dioxolane IV.

Step 4: The chlorine atom of IV is displaced by reaction with a benzoic acid salt in a compatible solvent such as dimethylformamide to give intermediate V.

Step 5: The benzoate ester function is then hydrolyzed under basic conditions to yield the desired end-product VI.

An alternate process for preparing further specific compounds of the present invention is illustrated in Flowsheet II:

Flowsheet II

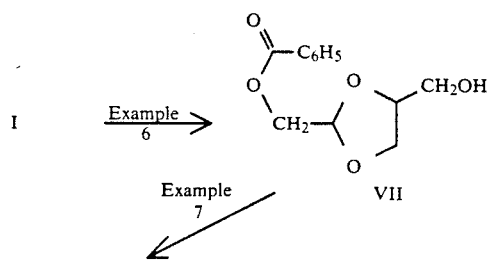

-continued
Flowsheet II
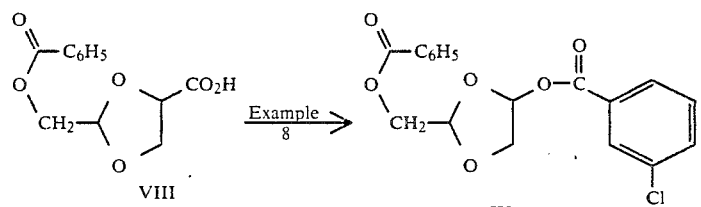
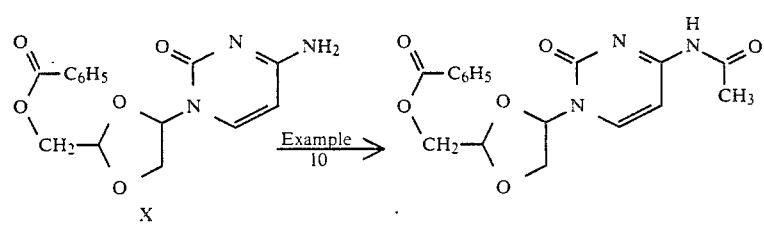
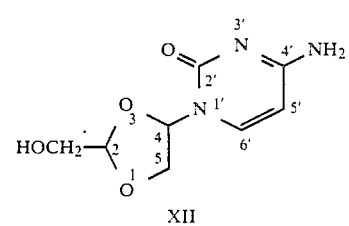
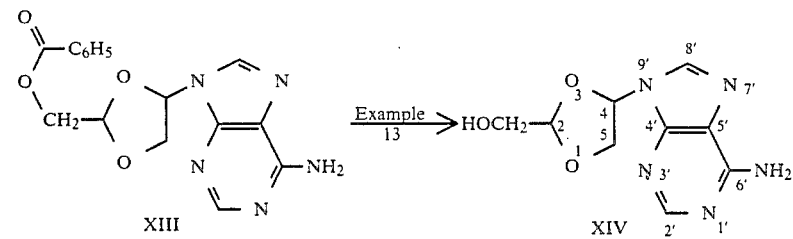
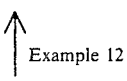
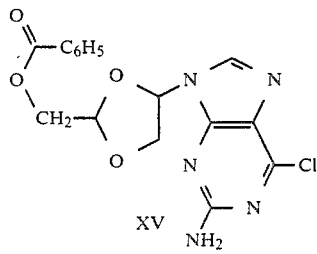

-continued
Flowsheet II

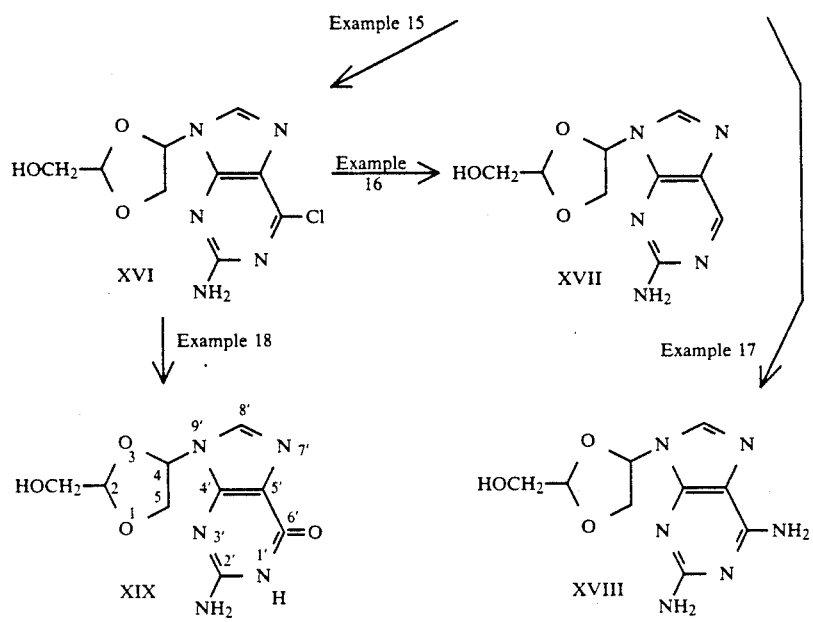

The various steps involved in the synthesis illustrated in Flowsheet II may be briefly described as follows:

Step 1: The chlorine atom of starting dioxolane I is displaced by a benzoic (or acetic) acid salt in a solvent such as dimethylformamide to yield the diol monoester VII.

Step 2: The hydroxymethyl group of VII is oxidized with a suitable reagent such as chromic acid (which may be complexed with pyridine) in a compatible organic solvent to give the dioxolane carboxylic acid VIII.

Step 3: The acid VIII is then submitted to Bayer-Villiger oxidation by the procedure outlined in Step 2 (Flowsheet I) above to give the corresponding aroyloxy-dioxolane IX.

Step 4: The key intermediate IX is reacted with cytosine previously sililated under the reaction conditions outlined in Step 3 (Flowsheet I) to give the cytsin-1'-yl dioxolane X.

Step 5: The amine function of X is acylated with acetic anhydride in pyridine to give XI which provides for easier separation of isomers.

Step 6: The ester and acetyl functions of XI are hydrolyzed under basic conditions to yield the desired end-product XII.

Step 7 (IX to XIII): Key intermediate IX is reacted with adenine by the procedure outlined above in Step 3 (Flowsheet I) to give XIII.

Step 8 (XIII to XIV): The ester function of XIII is hydrolyzed under basic conditions to yield the desired end-product XIV.

Step 9 (IX to XV): Intermediate IX is reacted with 2-amino-6-chloropurine under the conditions outlined in Step 3 (Flowsheet I) to give compound XV).

Step 10 (XV to XVI): The preceding intermediate is hydrolyzed under basic conditions to yield the desired end-product XVI.

Step 11 (XVI to XVII): The chlorine atom of XVI is removed by catalytic hydrogenation over Pd/C to give the 2'-amino-purin-9'-yl dioxolane XVII.

Step 12: The above intermediate XV is reacted with excess ammonia under pressure whereupon the 2',6'-diamino-purin-9'-yl dioxolane XVIII is generated.

Step 13: Compound XVI is submitted to boiling sodium hydroxide to give the desired end-product guanin-9'-yl dioxolane XIX.

ANTIVIRAL ACTIVITY

All of the compounds of the preferred embodiments are novel and some are valuable for their properties as non-toxic inhibitors of the primary replication of HIV-1 in previously uninfected T-lymphocytes over a prolonged period of time.

In particular, the compounds having the formula XII possess desirable properties, i.e. antagonism of HIV infectivity towards T-lymphocytes in the absence of cytotoxicity.

In vitro testing was conducted on the compounds to determined their inhibitory properties. Table 1 represents the results of a typical experiment. The figures reported are the micromolar concentrations in the incubation media which affect the ability of T-lymphocyte H-9 cells to be infected by HIV-1 following the protocol of H. Mitsuya and S. Broder, Proc. Natl. Acad. Sci. U.S.A, 1986, 83, 1911-1915; the level of infection being measured by the level of reverse transcriptase activity (RTA) as assayed in the usual manner with tritiated thymidine triphosphate (TTP). As a control drug, 2',3'-dideoxy-3'-azido-thymidine (AZT) was used and the RTA measured in the incubation medium after 8, 12 and 26 days of exposure to the inhibitor. The values in Table 1 reflect the total number of virus particles in the incubation medium.

TABLE 1

Example of the effects of prototype trans-XII, cis-XIV and AZT on ability of H-9 cells to be infected by HIV-1

| | | | RTA activity (cpm) after: | | |
|---|---|---|---|---|---|
| Expt. # | Inhibitor | Conc.[n] | 8 days | 12 days | 26 days |
| 1 | none | — | 198.612 | 327,570 | 239,019 |
| | trans-XII | 10 μM | 4.608 | 83,462 | 312,478 |

TABLE 1-continued

Example of the effects of prototype trans-XII, cis-XIV and AZT
on ability of H-9 cells to be infected by HIV-1

| Expt. # | Inhibitor | Conc.[n] | RTA activity (cpm) after: | | |
|---|---|---|---|---|---|
| | | | 8 days | 12 days | 26 days |
| | trans-XII | 50 μM | 1,319 | 758 | 1,732 |
| | AZT | 20 μM | 633 | 419 | 821 |
| 2 | none | — | 64,769 | 119,580 | 227,471 |
| | cis-XIV | 20 μM | 2,618 | 130,563 | 210,583 |
| | cis-XIV | 50 μM | 1,132 | 39,752 | 231,609 |
| | AZT | 20 μM | 587 | 1,316 | 679 |

It is apparent from the table that prototype compound trans-XII exhibits potent inhibitory activity. Other analogues displayed variable degrees of antiviral activity. Accordingly, as it is the rule for certain analogues of nucleosides, trans-XII and selected analogues are expected to demonstrate in vivo activity as inhibitors of retroviruses. Such compounds may also be used in combination with other antiviral agents at reduced doses, thus lowering their toxicity potential.

TOXICITY

In contrast to the results obtained with AZT or with other di-deoxynucleosides analogs, in vitro toxicity experiments showed that the compound trans-XII is non toxic even at concentration as high as 200 μM. In spite of the AZT activity, its serious bone marrow toxicity limits its therapeutic usefulness. It is then highly desirable to provide with new active antiviral agents which would be devoided of toxic side effects.

EXAMPLES

Example 1. Preparation of
2-chlorolmethyl-1,3-dioxolane-4-carboxylic acid (II)

Starting material I (40 g; prepared according to E. G. Hallonquist and H. Hibbert, Can. Res. J. 1933, 7, 129) was treated with pyridinium dichromate (PDC; 345 g) in dimethyl formamide (DMF; 690 ml) at 0° according to the procedure of E. J. Corey and G. Schmidt, Tetrahedron Lett., 1979, 399 and product II obtained as a crude mixture of cis- and trans-isomers (20 g) was identified by its $^1$H NMR spectrum [200 MHz, CDCl$_3$;tetramethyl silane (TMS) as internal reference]

δ(ppm): 3.6–3.8 (m,2H; CH$_2$Cl); 4.1–4.5 (m,2H; C$_5$H$_2$); 4.72–4.797 (qq,1H; C$_4$-H); 5.29–5.46 (tt,1H; C$_2$-H).

The product was used as such in the next step.

Example 2. Preparation of
2-chloromethyl-4-m.chlorobenzoyloxy-1,3-dioxolane (III)

The preceding product II (5.26 g) was treated in CH$_2$Cl$_2$ at −20° with 3.6 ml of ethyl chloroformate in the presence of 4.5 of triethylamine. To the solution was added 8.85 g of m.chloroperbenzoic acid at room temperature according to the procedure of D. H. R. Barton, I. H. Coates and P. G. Sammes, J. Chem. Soc., Perkin I, 1973, 599 to give III as a mixture of cis-and trans-isomers. These were separated and purified by flash chromatography on silica gel using a mixture of hexanes and ethyl acetate as the eluent. The isomers were identified by their $^1$H NMR spectra (recorded as in example 1):

trans-isomer of III: δ(ppm): 3.66 (q,2H; CH$_2$-Cl); 4.36 (qq,2H; C$_5$-H$_2$); 5.57 (t,1H; C$_2$-H); 6.7 (q,1H; C$_4$-H); 7.39–8.0 (m,4H; aromatic H).

cis-isomer of III: δ(ppm): 3.66 (q,2H; CH$_2$Cl); 4.24 (qq,2H; C$_5$-H$_2$); 5.43 (t,1H; C$_2$-H) 6.63 (q,1H; C$_4$-H); 7.42–8.04 (m,4H; aromatic H).

Example 3. Preparation of
2-chloromethyl-4-(thymin-1'-yl)-1,3-dioxolane (IV)

Reaction of the preceding compound with thymine was carried out according to the procedure of D. S. Wise and L. B. Townsend, in Nucleic Acid Chemistry, Eds. L. B. Townsend and R. S. Tipson, John Wiley & Sons, Inc., New Yord, 1978, Part I, pp 413–419. The product was a mixture of cis- and trans-isomers of IV (37.3 mg from 131 mg of III) which had the following $^1$H NMR characteristics (obtained as in example 1):

δ(ppm): 1.93 (d,3H; 5'-CH$_3$); 3.64 and 3.85 (dd,2H; CH$_2$Cl); 4.17–4.46 (m,2H; C$_5$-H$_2$); 5.26 and 5.72 (tt,1H; C$_2$-H); 6.6 and 6.66 (qq,1H; C$_4$-H); 7.40 and 7.49 (dd,1H; C$_6$'-H);

U.V.: (CH$_3$OH) I max. 264 nm.

Example 4. Preparation of
2-acetoxymethyl-4-(thymin-1'-yl)-1,3-dioxolane (V)

The preceding compound IV (35 mg) was reacted with anhydrous potassium acetate (70 mg) in boiling DMF (3 ml) for 4 h to give after conventional workup a cis- and trans-mixture of V (25 mg). These isomers were purified and separated by flash chromatography on silica gel using a mixture of hexanes and ethyl acetate as the eluent. Their $^1$H NMR spectra were as follows:

trans-isomer of V: δ(ppm): 1.94(d,3H; C$_5$''-CH$_3$); 2.12 (s,3H; CH$_3$-CO$_2$-); 4.05–4.43 (m,4H; C$_2$-CH$_2$-O$_2$CCH$_3$ and C$_5$-H$_2$); 5.65 (t,1H; C$_2$-H); 6.31 (q,1H; C$_4$-H); 7.14 (d,1H; C$_6$'-H); 8.18 (m,1H; N$_3$'-H).

cis-isomer of V: δ(ppm): 1.97 (d,3H; C$_5$'CH$_3$); 2.14 (s,3H; CH$_3$CO-O); 4.13–4.49 (m,4H; 2-CH$_2$OCOCH$_3$ and C$_5$H$_2$); 5.19 (t,1H; C$_2$-H); 6.40 (q,1H; C$_4$H); 7.43 (d,1H; C$_6$'-H); 8.12 (m,1H; N$_3$'-H).

U.V.: (CH$_3$OH) λmax. 264 nm.

Example 5. Preparation of
2-hydroxymethyl-4-(thymin-1'-yl)-1,3-dioxolane (VI)

The preceding trans- and cis-isomers of V (10 mg) were respectively treated with a catalytic amount of potassium carbonate in methanol (5 ml) at room temperature for 5–6 h and the mixture worked up in the usual manner and the respective products purified by flash chromatography on silica gel using a mixture of ethyl acetate and methanol as the eluent. The $^1$H NMR spectrum of the pure trans-isomer of VI was as follows (in CD$_3$COCD$_3$ as solvent);

trans-VI: δ(ppm): 1.87 (d,3H; C$_5$'-CH$_3$); 3.61 (q,2H; C$_2$-CH$_2$OH); 4.30 (qq,2H; C$_5$-H$_2$); 5.56 (t,1H; C$_2$-H); 6.31 (q,1H; C$_4$-H); 7.41 (d,1H; C$_6$'-H).

U.V.: (CH$_3$OH) λmax. 265 nm.cis-isomer of VI (in CD$_3$COCD$_3$):

δ(ppm): 1.82 (d,3H; C$_5$'-CH$_3$); 3.82 (q,2H; C$_2$CH$_2$OH); 4.24 (qq,2H; C$_5$-H$_2$); 5.02 (t,1H; C$_2$-H); 6.34 (q,1H; C$_4$-H); 7.81 (d,1H; C$_6$'-H).

U.V.: (CH$_3$OH) λmax. 264 nm.

Example 6. Preparation of
2-benzoyloxymethyl-4-hydroxymethyl-1,3-dioxolane (VIII)

Starting material I (41.6 g) was treated with potassium benzoate (65.56 g) in boiling dimethyl formamide containing 100 mg of 18-crown-6 for 24 h after which time the mixture was worked up in the usual manner and the product (51.02 g) characterized by its ¹H NMR spectrum (CDCl₃; TMS):

δ(ppm): 3.5–4.8 (m,7H; C₅-H₂, C₂-CH₂OCOC₆H₅, C₄-CH₂OH and C₂-H); 5.05 and 5.16 (tt,1H; C₄-H); 7.27–8.10 (m,5H; aromatic H).

Similar results were obtained using potassium acetate instead of potassium benzoate.

Example 7. Preparation of 2-benzoyloxymethyl-1,3-dioxolane-4-carboxylic acid (VIII)

The preceding compound VII (51.02 g) was treated at 0° with pyridinium dichromate (282.5 g) in dimethyl formamide (565 ml) and the mixture worked up in the usual manner to give 35 g of crude VIII which was used as such in the next example.

Example 8

A 10 g portion of crude VIII was treated with 6.03 ml of ethyl chloroformate in the presence of 8.6 ml of triethylamine followed by the addition of 16.81 g of m.chloroperbenzoic acid exactly as described in example 2 for the case of the preparation of intermediate III. The isomers of product IX thus obtained were purified by flash chromatography on silica gel using a mixture of hexanes and ethyl acetate as the eluent. They were characterized by their ¹H NMR spectra (CDCl₃):

trans-isomer of IX: δ(ppm): 4.29 (qq,2H; C₅-H₂); 4.49 (d,2H; C₂-CH₂OCOC₆H₅); 5.66 (t,1H; C₂-H); 6.70 (q,1H; C₄-H); 7.27–8.10 (m,9H; aromatic).

cis-isomer of IX: δ(ppm): 4.27 (qq,2H; C₅-H₂); 4.51 (d,2H; C₂-CHOCOC₆H₅); 5.51 (t,1H; C₂-H); 6.59 (d,1H; C₄-H); 7.26–8.09 (m,9H; aromatic).

Example 9. Preparation of 2-benzoyloxymethyl-4-(cytosin-1'-yl)-1,3-dioxolane (X).

Following the procedures described by T. Ueda and S. I. Watanabe, Chem. Pharm. Bull. (Japan), 1985, 33, 3689–3695 and by G. Gosselin, M. C. Bergogne, J. DeRudder, E. DeClercq and J. L. Imbach, J. Med. Chem., 1987, 30, 982–991, cytosine (139 mg) and either isomer of the preceding compound IX (363 mg) yielded a mixture of cis- and trans-isomers (390 mg) of X which was used as such in the following step.

Example 10

Treatment of cis- and trans-X with excess acetic anhydride in pyridine at room temperature yielded after work up in the conventional manner, a mixture of the cis- and trans-isomers of XI which were separated and purified by flash chromatography on silica gel using a mixture of hexanes and ethyl acetate as the eluent. They were characterized by their ¹H NMR spectra (CDCl₃):

trans-isomer of XI: δ(ppm): 2.15 (s,3H; C₄'-NH-COCH₃); 4.16 and 4.46 (m,4H; C₅-H₂ and C₂-CH₂OCOC₆H₅); 5.96 (t,1H; C₂-H); 6.24 (q,1H; C₄-H); 7.55–8.09 (m,5H; aromatic); 8.15 (d,1H; C₆'-H).

cis-isomer of XI: δ(ppm): 2.15 (s,3H; C₄'-NH-COCH₃); 4.26 and 4.56 (m,4H; C₅-H₂ and C₂-CH₂OCOC₆H₅); 5.35 (t,1H; C₄-H); 6.25 (q,1H; C₄-H); 7.18 (d,1H; C₅'-H); 7.58–8.04 (m,5H; aromatic); 8.17 (d,1H; C₆'-H).

Example 11. Preparation of cis- and trans-2-hydroxymethyl-4-(cytosin-1'-yl)-1,3-dioxolane (XII)

Each of the preceding isomers of XI (25 mg) was treated with potassium carbonate (20 mg) in methanol at room temperature for several hours and the mixtures worked up in the usual manner to yield each isomer of XII which were purified by chromatography on silica gel using a mixture of ethyl acetate and methanol as the eluent. They were crystallized from methanol and characterized by their respective ¹H NMR spectra (CD₃COCD₃):

| trans-isomer of XII: | |
|---|---|
| δ (ppm): | 3.62 (q, 2H; C₂—CH₂OH); |
| m.p. 179–180° | 4.21 (qq, 2H; C₅—H₂); |
| | 5.50 (t, 1H; C₂—H); |
| | 5.93 (d, 1H; C₅'—H, J = 7.5 Hz); |
| | 6.18 (q, 1H; C₄—H); |
| | 7.66 (d, 1H; C₆'—H, J = 7.5 Hz). |

U.V.: (CH₃OH) λmax. 271 nm. cis-isomer of XII:

| | |
|---|---|
| δ (ppm): | 3.82 and 4.15 (m, 4H; C₅—H₂ and C₂—CH₂OH); |
| m.p. 173–174° | 5.04 (t, 1H; C₂—H); |
| | 5.83 (d, 1H; C₅'—H); |
| | 6.23 (q, 1H; C₄—H); |
| | 8.05 (d, 1H; C₆'—H). |

U.V.: (CH₃OH) λmax. 270 nm.

Example 12. Preparation of 2-benzoyloxymethyl-4-(adenin9'-yl)-1,3-dioxolane (XIII)

Following the same procedure as in example 9, adenosine (135 mg) was coupled with either isomer of intermediate IX (545 mg) in dimethylformamide at 120° in the presence of trimethylsilyl triflate (0.45 ml) and the mixture worked up in the usual manner to yield a mixture of cis- and trans-isomers of XIII (540 mg) which were purified and separated by chromatography on silica gel using a mixture of hexanes and ethyl acetate as the eluent. They were characterized by their respective ¹H NMR spectra (CDCl₃): trans-isomer of XIII:

δ(ppm): 4.5 and 4.59 (m,4H; C₅-H₂ and C₂-CH₂OCOC₆H₅); 6.00 (t,1H; C₂-H); 6.65 (q,1H; C₄-H); 6.75 (m,2H; C₆'-H₂); 7.68–8.21 (m,5H; aromatic); 8.36 (s,1H; C₂'-H); 8.37 (s,1H; C₈'-H).

cis-isomer of XIII:
δ(ppm): 4.62 (d,2H; C₂-CH₂OCOC₆H₅); 4.65 (qq,2H; C₅-H₂); 5.52 (t,1H; C₂-H); 6.59 (q,1H; C₄-H); 6.85 (m,2H; C₆'-NH₂); 6.96–7.71 (m,5H; aromatic Hs); 7.66 (d,2H; C₂'-H and C₈'-H).

Example 13. Preparation of 2-hydroxymethyl-4-(adenin-9'-yl)-1,3-dioxolane (XIV)

Each isomer of the preceding compound XIII was treated with potassium carbonate in methanol at room temperature by the same procedure described in example 5 and each product purified by column chromatography on silica gel using a mixture of ethyl acetate and methanol as the eluent. The isomers were further purified by crystallization from methanol and characterized by their ¹H NMR spectra (CD₃SOCD₃):

trans-isomer of XIV:

δ(ppm): 3.50 (d,2H; C$_2$-CH$_2$OH); 4.70 (m,2H; C$_5$-H$_2$); 5.52 (t,1H; C$_2$-H); 6.44 (q,1H; C$_4$-H); 8.18 (s,1H; C$_{2'}$-H); 8.31 (s,1H; C$_{8'}$-H).

U.V.: (CH$_3$OH) λmax. 269 nm.

cis-isomer of XIV:

δ(ppm): 4.63 (d,2H; C$_2$-CH$_2$OH); 4.29 (qq,2H; C$_5$-H$_2$); 5.08 (,1H; C$_2$-H); 6.43 (q,1H; C$_4$-H); 8.18 (s,1H; C$_{2'}$-H); 8.36 (s,1H; C$_{8'}$-H).

U.V.: (CH$_3$OH) λ269 nm.

Example 14. Preparation of 2-benzoyloxymethyl-4-(2'-amino-6'-chloro-purin-9'-yl)-1,3-dioxolane (XV)

A solution of 2-amino-6-chloropurine (600 mg; 3.54 mmol) in 20 ml of hexamethyldisilazane (HMDS) containing 0.5 ml of trimethylsilyl chloride (TMS-Cl) was heated under reflux for 3 h after which time the mixture was evaporated to dryness in vacuo. The residue was dissolved in 75 ml of dichloroethane containing 910 mg of compound IX and 0.6 ml of trimethylsilyl triflate (TMS-Tf) added. After refluxing under argon for 4 h, the mixture was cooled, 2 g of solid NaHCO$_3$ added followed by 50 ml of saturated aqueous NaHCO$_3$. The organic layer was collected and after work-up in the usual manner, crude XV was obtained as an oil which was purified and separated into its isomers by chromatography on silica gel using hexane-ethyl acetate (3:7) as the eluent to give 230 mg of pure trans-and 250 mg or pure cis-isomer as colorless foams. They were characterized by their $^1$H NMR spectra (CDCl$_3$): trans-isomer of XV (Rf: 0.40; hexane-EtOAc 3:7):

δ(ppm): 4.45–4.52 (m,4H; C$_5$-H$_2$, C$_2$-CH$_2$OCOC$_6$H$_5$); 5.16 (b,2H; C$_{2'}$-NH$_2$); 5.83 (t,1H; C$_2$-H, J=3.8 Hz); 6.39 (dd,1H; C$_4$-H); 7.41–7.58 (m,3H; aromatic); 7.92 (s,1H; C$_{8'}$-H); 8.06 (d,2H; aromatic, J=7 Hz).

U.V.: (CH$_3$OH) λmax. 312 nm.

cis-isomer of XV (Rf: 0.26, hexane-EtOAc 3:7):

δ(ppm): 4.25–4.33 (dd,1H; C$_5$-H, J=5.43 Hz); 4.59–4.64 (m,3H; C$_5$-H and C$_2$-CH$_2$-OCOC$_6$H$_5$); 5.17 (b,2H; C$_{2'}$-NH$_2$); 5.42 (t,1H; C$_2$-H, J=3.50 Hz); 6.33–6.53 (dd,1H; C$_4$-H); 7.38–7.57 (m,3H; aromatic); 7.93–7.98 (d,2H; aromatic); 8.00 (s,1H; C$_{8'}$-H).

U.V.: (CH$_3$OH) λmax. 312 nm.

Example 15. Preparation of trans- and cis-2-hydroxymethyl-4-(2'-amino-6'-chloro-purin-9'-yl)-1,3-dioxolane (XVI)

The preceding trans-isomer of XV (180 mg) was dissolved in 30 ml of methanol, the solution cooled to 0 and dry ammonia bubbled through for 15 min. After stirring at room temperature for 15 h, the solvent was removed in vacuo and the residue crystallized from ether. After recrystallization from ethanol-ether, 98 mg of pure trans-XVI, m.p. 155°–156°, was obtained (Rf: 0.23, EtOAc). It was characterized by $^1$H NMR (DMSO-d$_6$):

trans-XVI: δ(ppm): 3.44–3.49 (m,2H; C$_2$-CH$_2$OH); 4.37–4.45 (m,2H; C$_5$-H$_2$); 5.01 (t,1H; C$_5$-CH$_2$OH, J=6.2 Hz); 5.46 (t,1H; C$_2$-H, J=3.6 Hz); 6.27–6.32 (dd,1H; C$_4$-H, J=4.1 Hz); 7.00 (b,2H; C$_{2'}$-NH$_2$); 8.26 (s,1H; C$_{8'}$-H).

U.V.: (CH$_3$OH) λmax. 247 and 308 nm.

The cis-isomer of XVI was obtained in similar yield from the cis-isomer of XV by the same preceding procedure. After recrystallization from ethanol-ether, the pure product had m.p. 145°–147° (Rf: 0.24, EtOAc). It was characterized by $^1$H NMR (DMSO-d$_6$):

cis-XVI: δ(ppm): 3.54–3.59 (m,2H; C$_2$-CH$_2$OH); 4.12–4.19 (dd,1H; C$_5$-H, J=5.3 Hz and 9.8 Hz); 4.48–4.53 (d,1H; C$_5$-H, J=9.8 Hz); 5.01 (t,1H; C$_2$-H, J=2.8 Hz); 5.09 (t,1H; C$_2$-CH$_2$-OH, J=6.0 Hz); 6.24 (d,1H; C$_4$-H, J=5.1 Hz); 6.96 (b,2H; C$_{2'}$-NH$_2$); 8.23 (s,1H; C$_{8'}$-H).

U.V.: (CH$_3$OH) λmax. 247 and 308 nm.

Example 16. Preparation of trans- and cis-2-hydroxymethyl-4-(2'-amino-purin-9'-yl)-1,3-dioxolane (XVII)

The preceding trans-isomer of XVI (50 mg) was submitted to hydrogenation conditions under 50 psi of hydrogen over 10% Pd/c (30 mg) in 30 ml of ethanol containing 0.5 ml of triethylamine. After 3 h of shaking, the mixture was worked up in the usual manner to yield a solid which was recrystallized from ethanol-ether to give 36 mg of pure trans-XVII, m.p. 153°–155°, Rf: 0.25 (EtOAc: MeOH 85:15). It was characterized by $^1$H NMR (DMSO-d$_6$):

trans-XVII: δ(ppm): 3.44–3.49 (m,2H; C$_2$-CH$_2$OH); 4.38–4.44 (m,2H: C$_5$-H$_2$); 4.99 (t,1H; C$_2$-CH$_2$-OH, J=6.1 Hz); 5.45 (t,1H; C$_2$-H, J=3.6 Hz); 6.29–6.34 (dd,1H; C$_4$-H); 6.59 (b,2H; C$_{2'}$-NH$_2$); 8.19 (s,1H; C$_{8'}$-H); 8.59 (s,1H; C$_{6'}$-H).

The cis-isomer of XVII was obtained in similar yield from the cis-isomer of XVI by the same preceding procedure. After recrystallization from ethanol-ether, the pure product had m.p. 145°–148°, Rf: 0.25 (EtOAc:-MeOH 85:15). It was characterized by $^1$H NMR (DMSO-d$_6$):

cis-XVII: δ(ppm): 3.55–3.60 (dd,2H; C$_2$-CH$_2$OH, J=2.10 and 6.1 Hz); 4.14–4.22 (dd,1H; C$_5$-H, J=5.4 and 9.7 Hz); 4.47–4.53 (dd, 1H; C$_5$-H, J=1.38 and 9.7 Hz); 5.02 (t,1H; C$_2$-H, J=3 Hz); 5.11 (t,1H; C$_2$-CH$_2$OH, J=7.2 Hz); 6.58 (b,2H; C$_{2'}$-NH$_2$); 8.19 (s,1H; C$_{8'}$-H); 8.57 (s,1H; C$_{6'}$-H).

U.V.: (CH$_3$OH) λmax. 255, 308 nm.

Example 17. Preparation of trans- and cis-2-hydroxymethyl-4-(2', 6'-diamino-purin-9'-yl)-1,3-dioxolane (XVIII)

The above compound trans-XV (200 mg) was dissolved in 30 ml of methanol saturated at 0° with dry ammonia and the solution heated in a steel bomb to 105°–110° for 16 h. The solution was evaporated to dryness and the residue purified by chromatography on silica gel using chloroform-methanol 4:1 as the eluent to give 101 mg of product which was recrystallized from methanol-ether to yield pure trans-XVIII, m.p. 165°–168°, Rf: 0.30 (CHCl$_3$:CH$_3$OH 4:1). It was characterized by $^1$H NMR (DMSO-d$_6$):

trans-XVIII: δ(ppm): 3.43–3.48 (m,2H; C$_2$-CH$_2$OH); 4.34–4.49 (m,2H; C$_5$-H$_2$); 4.97 (t,1H; C$_2$-CH$_2$OH); 5.42 (t,1H; C$_2$-H); 5.82 (b,2H; C$_{2'}$- or C$_{6'}$-NH$_2$) 6.18–6.23 (dd,1H; C$_4$-H); 6.72 (b,2H; C$_{2'}$- or C$_{6'}$-NH$_2$); 7.84 (s,1H; C$_{8'}$-H).

U.V.: (CH$_3$OH) λmax. 255, 280 nm.

The cis-isomer of XVIII was obtained by the same preceding procedure from compound cis-XV. After recrystallization from methanol-ether, pure cis-XVIII, m.p. 180°–182°, Rf: 0.32 (CHCl$_3$-CH$_3$OH 4:1) was obtained in a similar yield. It was characterized by $^1$H NMR (DMSO-d$_6$):

cis-XVIII: δ(ppm): 3.56–3.58 (d,2H; C$_2$-CH$_2$OH, J=4.2 Hz); 4.11–4.19 (dd,1H; C$_5$-H, J=4.5 and 9.7 Hz); 4.38–4.44 (dd,1H; C$_5$-H, J=1.6 and 11.2 Hz); 5.00 (t,1H; C$_2$-H, J=3.1 Hz); 5.91 (b,2H; C$_{2'}$- or C$_{6'}$-NH$_2$);

6.15-6.19 (dd,1H; C$_4$-H); 6.84 (b,2H; C$_2'$- or C$_6'$-NH$_2$); 7.86 (s,1H; C$_8'$-H).

U.V.: (CH$_3$OH) λmax. 254,279 nm.

Example 18. Preparation of cis- and trans-2-hydroxymethyl-4-(guanin-9'-yl)-1,3-dioxolane (XIX)

The above cis-XVI (40 mg) was dissolved in a mixture of 15 ml of methanol, 2 ml of water and 2 g of sodium hydroxide and the solution heated under reflux for 5 h after which time it was diluted with 100 ml of water and excess pyridinium sulfonate resin added. The slurry was filtered, the resin washed with water and the combined aqueous filtrates evaporated to dryness in vacuo to leave a residue which was taken up in 50% aqueous methanol. The solution was treated with activated charcoal, filtered and the filtrate evaporated to dryness in vacuo to give a solid residue that was recrystallized from ethanol-water to yield pure cis-XIX (27 mg) m.p.>250° decomp., Rf: 0.23 (CHCl$_3$:CH$_3$OH 7:3). It was characterized by $^1$H NMR (DMSO-d$_6$):

cis-XIX: δ(ppm): 3.55 (m,2H; C$_2$-CH$_2$OH); 4.10-4.17 (dd,1H; C$_5$-H, J=5.6 and 9.8 Hz); 4.37-4.42 (dd,1H; C$_5$-H, J=1.4 and 9.6 Hz); 4.98 (t,1H; C$_2$-H, J=3.2 Hz); 5.15 (b,1H; C$_2$-CH$_2$OH); 6.10-6.13 (dd,1H; C$_4$-H, J=2.4 and 5.3 Hz); 6.66 (b,2H; C$_2'$-NH$_2$); 7.78 (s,1H; C$_8'$-H); 11.02 (b,1H; N$_1'$-H).

U.V.: (CH$_3$OH) λmax. 252,270 (shoulder).

The isomer trans-XIX was obtained in similar yield from the above trans-XVI by the same preceding procedure. After recrystallization from ethanol-water, pure trans-XIX, m.p.>260° (dec.), Rf: 0.23 (CHCl$_3$:CH$_3$OH 7:3) was obtained and characterized by $^1$H NMR (DMSO-d$_6$):

trans-XIX: δ(ppm): 3.42-3.47 (m,2H; C$_2$-CH$_2$OH); 4.34 (d,2H; C$_5$-H$_2$, J=4.8 Hz); 4.99 (t,1H; C$_2$-CH$_2$OH); 5.40 (t,1H; C$_2$-H, H=3.5 Hz); 6.15-6.20 (t,1H; C$_4$-H, J=4.8 Hz); 6.49 (b,2H; C$_2'$-NH$_2$); 7.83 (s,1H; C$_8'$-H); 10.64 (b,1H; N$_1'$-H).

U.V.: (CH$_3$OH) λmax. 252,270 (shoulder).

We claim:

1. A 1,3-dioxolane derivative of the general formula L, the geometric and optical isomers thereof and mixtures of these isomers:

$$R_1OCH_2-\underset{O}{\overset{O}{\diamond}}-R_2 \quad (L)$$

wherein:
R$_1$ is selected from the group consisting of hydrogen, an aliphatic acyl group having 2 to 16 carbon atoms, benzoyl and a benzoyl substituted in any position by a halogen, a lower alkyl, a lower alkoxy, a nitro or a trifluoromethyl group;
R$_2$ is a heterocyclic radical selected from:

[Three heterocyclic structures showing cytosine-like, thymine-like, and uracil-like bases with substituents R$_3$, R$_4$, and R$_5$]

wherein
R$_3$ is selected from the group consisting of hydrogen and lower alkyl radicals having from 1 to 3 carbon atoms;
R$_4$ is selected from the group consisting of hydrogen, lower alkyl or alkenyl radicals having from 1 to 3 carbon atoms; and
R$_5$ is selected from the group consisting of lower alkyl or alkenyl radicals having from 1 to 3 carbon atoms, fluoro and iodo.

2. The compound of claim 1, which is the 2-acetoxymethyl-4-(thymin-1'-yl)-1,3-dioxolane.

3. The compound of claim 1 which is the 2-hydroxymethyl-4-(thymin-1'-yl)-1,3-dioxolane.

4. The compound of claim 1 which is the 2-benzoyloxymethyl-4-(cytosin-1'-yl)-1,3-dioxolane.

5. The compound of claim 1 which is the trans-2-hydromethyl-4-(cytosin-1'-yl)-1,3-dioxolane.

6. A method for treating retroviral infections by administering to an infected host a therapeutically effective amount of a 2-substituted-4-substituted-1,3-dioxolane of Formula (L), the geometric and optical isomers thereof, and mixtures of those isomers:

$$R_1OCH_2-\underset{O}{\overset{O}{\diamond}}-R_2 \quad (L)$$

wherein:
R$_1$ is selected from the group consisting of hydrogen, an aliphatic acyl group having 2 to 16 carbon atoms, benzoyl and a benzoyl substituted in any position by a halogen, a lower alkyl, a lower alkoxy, a nitro or a trifluoromethyl group;
R$_2$ is a heterocyclic radical selected from:

[Three heterocyclic structures showing cytosine-like, thymine-like, and uracil-like bases with substituents R$_3$, R$_4$, and R$_5$]

wherein
R$_3$ is selected from the group consisting of hydrogen and lower alkyl radicals having from 1 to 3 carbon atoms;
R$_4$ is selected from the group consisting of hydrogen, lower alkyl or alkenyl radicals having from 1 to 3 carbon atoms; and
R$_5$ is selected from the group consisting of lower alkyl or alkenyl radicals having from 1 to 3 carbon atoms, fluoro and iodo.

* * * * *